US008586292B2

(12) United States Patent
Sarkar et al.

(10) Patent No.: US 8,586,292 B2
(45) Date of Patent: Nov. 19, 2013

(54) METHODS FOR IDENTIFYING COMPOUNDS FOR TREATMENT OF THROMBOTIC CONDITION

(75) Inventors: Sibaji Sarkar, Allston, MA (US); Jane Freedman, Wellesley, MA (US); Sonia Varghese, Boston, MA (US)

(73) Assignee: Sibaji Sarkar, Allston, MA (US)

( * ) Notice: Subject to any disclaimer, the term of this patent is extended or adjusted under 35 U.S.C. 154(b) by 385 days.

(21) Appl. No.: 12/979,753

(22) Filed: Dec. 28, 2010

(65) Prior Publication Data
US 2011/0124512 A1 May 26, 2011

Related U.S. Application Data

(62) Division of application No. 10/537,599, filed as application No. PCT/US03/38374 on Dec. 4, 2003, now abandoned.

(60) Provisional application No. 60/431,633, filed on Dec. 6, 2002.

(51) Int. Cl.
*C12Q 1/00* (2006.01)
(52) U.S. Cl.
USPC .................................................. 435/4
(58) Field of Classification Search
USPC ............................................. 435/4; 514/14.9
See application file for complete search history.

(56) References Cited

U.S. PATENT DOCUMENTS

| | | | |
|---|---|---|---|
| 6,191,103 B1 * | 2/2001 | Shohet et al. | 514/14.9 |
| 6,432,963 B1 | 8/2002 | Hisamichi et al. | |
| 6,448,245 B1 | 9/2002 | DePetrillo et al. | |
| 6,649,591 B2 | 11/2003 | Lai | |
| 2002/0128434 A1 | 9/2002 | Zimmerman et al. | |
| 2006/0127385 A1 * | 6/2006 | Sarkar et al. | 424/94.2 |
| 2006/0188503 A1 * | 8/2006 | Shen et al. | 424/145.1 |
| 2010/0305206 A9 * | 12/2010 | Messadek | 514/554 |

FOREIGN PATENT DOCUMENTS

| | | |
|---|---|---|
| EP | 0456835 B1 | 5/1996 |
| GB | 2276384 A | 9/1994 |
| WO | 93/00095 | 1/1993 |
| WO | 93/08174 | 4/1993 |
| WO | 94/08962 | 4/1994 |
| WO | 94/12478 | 6/1994 |

OTHER PUBLICATIONS

Chakrabarti S. et al. Glycoprotein IIb/IIIa Inhibition Enhances Platelet Nitric Oxide Release. Thrombosis Research 113(3-4)225-233, 2004.*
Tanus-Santos J. et al. Effects of eNOS Gene Polymorphisms . . . Pharmacogenetics 12(5)407-413, Jul. 2002.*
Zulli A. et al. A Novel Immunohistochemical Semiquantitative Technique . . . J of Histochemistry & Cytochemistry 46(2)257-262, 1998.*
Randriamboavonjy V. et al. Endothelial Nitric Oxide Synthase in Platelets . . . Pharmacological Reports 57:Suppl 59-65, 2005.*
Predescu D. et al. Constitutive eNOS Derived Nitric Oxide is a Determinant of Endothelial Junctional Integrity. Am J Physiol Lung Cell Mol Physiol 289:L371-L381, 2005.*
Collen and Lijnen, Blood 78:3114 (1991).
Goto et al., Circulation 106:266-72 (2002).
Maguire et al., Proteomics 2:642-8 (2002).
Blackburn and Gadek, "Chapter 9. Glycoprotein IIb/IIIa Antagonists", Annual Reports in Medicinal Chemistry—28, Section II—Cardiovascular and Pulmonary Agents, pp. 79-88, 1993, publ. by Academic Pres, Inc.
Sarkar et al., Biochem. J. 338:677-80 (1999).
Sprengers and Kluft, Blood 69:381 (1987).
McDowell, et al., J. Am. Chem. Soc. 1994, 116, pp. 5069-5076.

* cited by examiner

*Primary Examiner* — Ralph Gitomer
(74) *Attorney, Agent, or Firm* — Nixon Peabody LLP; Ronald I. Eisenstein; Leena H. Karttunen Contarino

(57) ABSTRACT

The present invention is directed to methods for sustaining eNOS activity to inhibit platelet aggregation, clot retraction, and enhance fibrinolysis. One embodiment of the invention provides methods of treating thrombosis by inhibiting the activity of the syk kinase. Another embodiment provides assays for the discovery of improved compounds to treat thrombosis, by screening for compounds which sustain eNOS activity. Yet another embodiment provides assays for the discovery of improved compounds to treat thrombosis, by identifying inhibitors of calpain and IIbIIIa by screening for compounds which act through calpain or IIbIIIa to sustain eNOS activity. Yet another embodiment provides for enhancing fibrinolysis, by inhibiting the activity of the syk kinase or calpain.

7 Claims, 3 Drawing Sheets

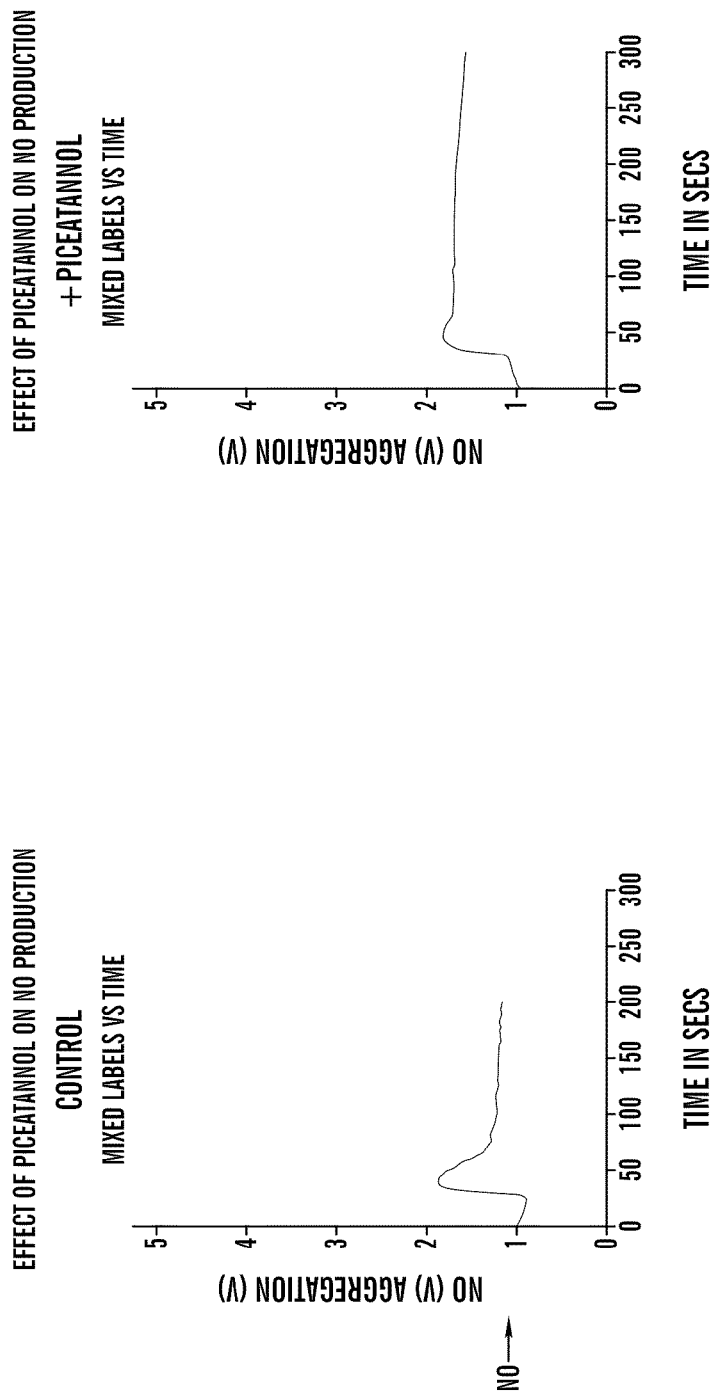

METHODS FOR IDENTIFYING COMPOUNDS FOR TREATMENT OF THROMBOTIC CONDITION

CROSS-REFERENCE TO RELATED APPLICATION

This application is a divisional application under 35 U.S.C. §120 of a U.S. application Ser. No. 10/537,599, now abandoned, which is a 371 National Stage of International Application No. PCT/US2003/038374 filed on Dec. 4, 2003, which designated the U.S., and which claims the benefit under 35 U.S.C. 119(e) of U.S. Provisional Patent Application Ser. No. 60/431,633, filed Dec. 6, 2002.

FIELD OF THE INVENTION

The present application is directed to methods and kits for sustaining eNOS activity. These methods and kits can be used to treat thrombosis by inhibiting platelet aggregation and clot retraction, and enhancing fibrinolysis.

BACKGROUND OF THE INVENTION

Intravascular thrombosis is one of the most frequent pathological events and a major cause of morbidity and mortality. Critical steps in the development of acute coronary syndromes are the disruption, rupture, or erosion of artherosclerotic plaques with the formation of either partially or completely occlusive thrombus. Factors that stimulate thrombosis include vascular damage, stimulation of platelets, and activation of the coagulation cascade. Platelet adhesion to the exposed subendothelial surfaces of injured blood vessels, with subsequent platelet activation, and the resulting platelet-rich clot formation have been shown to be associated with various pathological conditions. The most prevalent vascular disease states are related to platelet dependent narrowing of the blood supply such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis or abrupt closure following angioplasty, carotid endarterectomy, anastomosis of vascular grafts, and etc. These conditions represent a variety of disorders thought to be initiated by platelet activation on vessel walls.

Platelets play a central role in blood clotting and blood vessel repair, rapidly adhering to sites of vessel damage where they undergo dramatic shape change to spread over the injury site. In addition to these physical changes during blood vessel injury, platelets also undergo a number of biochemical changes that must be tightly regulated. Regulation of platelets ensures that the formation of a blood clot is of sufficient size to seal off the damaged area, preventing blood loss, while not disrupting blood flow to vital organs by causing vessel occlusion.

Platelet aggregation refers to the adherence of platelets to each other, typically at the site of blood vessel damage. Clot retraction describes the contractile ability of platelets to consolidate or shrink the size of the blood clot once it has formed. This process is thought to be important for both maintenance of the vasculature and also the subsequent manner in which the blood clot is removed once wound healing has finished. Fibrinolysis, also known as clot lysis, refers to the process through which thrombi dissolve, as a consequence of activation of the fibrinolytic system.

Platelet aggregation, clot retraction, and fibrinolysis are important parts of thrombus regulation.

While clotting as a result of an injury to a blood vessel is a critical physiological process for mammals such as man, inappropriate clotting can also lead to disease states. For example, a pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

Nitric oxide (NO) plays an important role during thrombus formation. During platelet aggregation and clot retraction, both inducible nitric oxide synthase (NOS) and constitutive nitric oxide synthase (eNOS) are transiently activated and then deactivated. The activity of nitric oxide (NO) as a vasodilator has been known for well over 100 years. (NO) is produced by NO synthases (NOS), which oxidize L-arginine to L-citrulline. It has recently become apparent that there are at least three types of NO synthase: (i) a constitutive, Ca++/calmodulin dependent enzyme, located in the endothelium, that releases NO in response to receptor or physical stimulation (eNOS); (ii) a constitutive, Ca++/calmodulin dependent enzyme, located in the brain, that releases NO in response to receptor or physical stimulation; and (iii) a Ca++ independent enzyme which is induced after activation of vascular smooth muscle, macrophages, endothelial cells, and a number of other cells by endotoxin and cytokines (NOS). All three NOS isoforms have a similar molecular structure and require multiple cofactors.

Given the role of NO during platelet aggregation, regulation of its synthesis has direct implications for platelet function during thrombus formation and acute coronary syndromes. More particularly, the ability to sustain NO production and release correlates with the inhibition of platelet aggregation and clot retraction.

For example, it has recently been shown that calpeptin, an inhibitor of the cellular protease calpain, can inhibit inducible NOS and inhibit platelet aggregation. Furthermore, U.S. patent application Ser. No. 09/953,590, filed Sep. 14, 2001 and published as US 2002/0128434A1, discloses that certain calpain inhibitors are useful as inhibitors against aggregation of platelets caused by thrombin. Similarly, inhibition of calpains for treating thrombosis or thrombotic platelet aggregation is described in U.S. patent application Ser. No. 09/847,872, filed May 2, 2001 and published as US 2002/0115665. U.S. Pat. No. 6,448,245, issued Sep. 10, 2002, provides methods and compounds for inhibiting calpains. However, while activity has focused on inducing nitric oxide synthase activity, it has not been previously known how to regulate constitutive endothelial nitric oxide synthase (eNOS) activity.

Integrin-mediated platelet adhesion triggers signal transduction cascades involving translocation of proteins and tyrosine phosphorylation events, ultimately causing large signaling complexes to be assembled. This activity is mediated by a number of platelet adhesive glycoproteins. The binding sites for fibrinogen, fibronectin, and other clotting factors have been located on the platelet membrane glycoprotein complex IIb/IIIa. When a platelet is activated by an agonist such as thrombin, the GPIIb/IIIa binding site becomes available to fibrinogen, eventually resulting in platelet aggregation and clot formation. Thus, the surface integrin GPIIb/IIIa (also known as the platelet integrin $\alpha_{IIb}\beta_3$) plays a key role during platelet aggregation.

A number of approaches have been taken to block platelet aggregation by disrupting the binding of fibrinogen to its receptor, IIb/IIIa. Examples of agents that inhibit their interaction include for example various benzoic acid and phenylacetic acid (see U.S. Pat. No. 5,039,805); seven membered ring containing bicyclic compounds (see PCT International patent application WO 93/00095); bicyclic compounds having fused six membered rings (quinazoline-3-alkanoic acid derivates) (see EP 456835); nonpeptidyl integrin inhibitors which are bicyclic 6 and 7 membered fused ring systems (see PCT International patent application WO 93/08174); 6,5-bicyclic compounds (Patent Application WO94/12478 and Patent Application WO94/08962); novel oxoquinazolin derivatives (see British Patent application GB 2276384). Furthermore, the design of non-peptidal inhibitors of fibrinogen-glycoprotein IIb/IIIa binding has been described (see McDowell, et. al., J. Am. Chem. Soc. 1994, 116, pp. 5069-5076 and Blackburn and Gadek, "Chapter 9. Glycoprotein IIb/IIIa Antagonists", Annual Reports in Medicinal Chemistry—28, Section II—Cardiovascular and Pulmonary Agents, pp 79-88, 1993, publ. by Academic Pres, Inc.).

One signaling molecule activated during platelet activation is the cellular kinase syk. Maguire et al., *Proteomics* 2:642-8 (2002) discloses the identification of syk as one of several phosphotyrosine proteins present in thrombin-activated platelets. syk can be immunoprecipitated from platelets stimulated by von Willebrand factor and ristocetin, modeling platelet adhesion and thrombus formation [Goto et al., *Circulation* 106:266-72 (2002)]. For example, syk associates directly with the integrin $\alpha_{IIb}\beta_3$ in platelets, demonstrating that $\alpha_{IIb}\beta_3$-associated syk is activated during platelet stimulation [Sarkar et al., Biochem. J. 338:677-80 (1999)].

Anti-thrombotic agents can block or inhibit thrombus formation, as discussed above; however, they are not very effective in dissolving a pre-formed thrombus or to help in fibrinolysis. Thus, terminal thrombus formation may cause myocardial infarction and/or ischemic chest pain. Instead, the current treatment for total blockage by thrombus formation is either angio-balloon-plasty and/or bypass surgery.

A number of agents which promote fibrinolysis after a thrombus has been formed have been identified. Fibrinolysis is promoted by the conversion of plasminogen to plasmin. The most important agents are the physiologic plasminogen activators tissue-type plasminogen activator (t-PA) and urokinase-type plasminogen activator (u-PA). t-PA and u-PA are serine proteinases that activate the proenzyme plasminogen to the broad specificity enzyme plasmin. [Collen and Lijnen, *Blood* 78:3114 (1991)]

However, fibrinolytic agents typically have problems because of the inhibitory effect of platelets on clot lysis. Activated platelets at sites of thrombus secrete agents which inhibit proteolytic processing of plasminogen to active plasmin. The serpin plasminogen activator inhibitor-1 (PAI-1) is the main inhibitor of both t-PA and u-PA, and constitutes a critical regulator of plasminogen activation. [Sprengers and Kluft, *Blood*:69:381 (1987)] Several animal and clinical studies have associated elevations in plasma PAI-1 with increased risk for thrombosis, whereas a drop in plasma PAI-1 levels may be a cause of recurrent bleeding.

During fibrinolysis, plasmin is very rapidly and specifically inhibited by alpha$_2$-antiplasmin ($\alpha_2$-AP), which circulates in plasma at a high concentration of 1 μmol/L. Whereas $\alpha_2$-AP is synthesized in the liver and released into the circulation, the origin of active PAI-1 in the circulation is less well-defined. PAI-1 is produced by several cell types, including endothelial cells, smooth muscle cells, fibroblasts, and hepatocytes. Two distinct pools of PAI-1 exist in the circulation, one in platelets and one in plasma. Human platelets are a major reservoir of PAI-1, with up to 90% of the circulating human PAI-1 contained within platelet α-granules, yielding up to 700 ng PAI-1 per $10^9$ platelets. However, platelet PAI-1 exists predominantly in a latent or inactive form, suggesting its effect on fibrinolysis to be rather limited. Nevertheless, the inhibitory effect of platelets on clot lysis was proposed to be mediated partly by platelet PAI-1, a conclusion supported by differential clot lysis efficiency in the presence of normal platelets or platelets derived from PAI-1-deficient patients.

There is a need in the area of cardiovascular and cerebrovascular therapeutics for alternative agents which can be used in the prevention and treatment of thrombi. Accordingly, it would be desirable to have improved methods for treating thrombosis. More particularly, it would be desirable to have improved compounds to inhibit platelet aggregation and clot retraction, and promote fibrinolysis. There is also a need to have better assays for screening for such compounds.

SUMMARY OF THE INVENTION

The present invention provides methods and kits for sustaining constitutive eNOS activity to inhibit platelet aggregation and clot retraction and promote fibrinolysis. We have now shown that there are three different routes to sustain constitutive eNOS activity: (1) by inhibiting the activity of the syk kinase; (2) by inhibiting calpain; and (3) by using an antagonist of IIbIIIa.

One embodiment of the invention provides means for inhibiting the activity of the syk kinase. This can then be used to treat thrombosis.

Another embodiment of the present invention provides assays for the discovery of improved compounds to treat thrombosis, by screening for compounds which sustain constitutive eNOS activity.

Another embodiment of the present invention provides assays for the discovery of improved compounds to treat thrombosis, by identifying inhibitors of calpain and IIbIIIa by screening for compounds which act through calpain or IIbIIIa to sustain constitutive eNOS activity.

Yet another embodiment provides methods for treating or preventing thrombosis by promoting fibrinolysis by inhibiting the activity of the syk kinase or calpain.

BRIEF DESCRIPTION OF THE DRAWINGS

FIGS. 3A and 3B show the effect of piceatannol on NO production. Platelets at $2\times10^8$/ml were pre-incubated with either piceatannol at final concentration 2.5 ug/ml or vehicle DMSO for 30 minutes in the dark. To a final volume of 0.5 ml, fibrinogen was added to a final concentration of 1 mg/ml, 1 mM $Ca^{2+}$, and 2 mM $Mg^{2+}$, and GPRP to a final concentration of 20 µM. The tube was placed in the NO-501 monitor to measure NO production and the platelets are stirred with a magnetic stirrer. TRAP (Thrombin Receptor Agonist Peptide) at a final concentration of 20 µM was added to start the reaction.

DETAILED DESCRIPTION OF THE INVENTION

Figure 1:
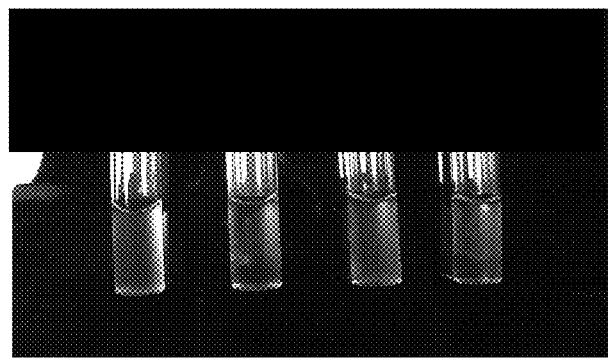
FIG. 1 shows the effect of a syk kinase inhibitor, piceatannol, on clot retraction. Platelets ($2 \times 10^8$ platelets/ml) were incubated with either piceatannol at a final concentration of 40 μg/ml, calpeptin at a final concentration of 200 μg/ml, or vehicle DMSO for 30 minutes in the dark. To each sample, fibrinogen was added to a final concentration of 300 nM, 1 mM $Ca^{2+}$, and 2 mM $Mg^{2+}$, 10 minutes prior to the addition of 0.5 unit/ml of thrombin. The clots were incubated for 30 minutes at 37° C. and then transferred to ice before taking photographs. Tubes: 1, vehicle control treated sample without the addition of thrombin; 2, vehicle control treated sample; 3, piceatannol treated sample; 4, calpeptin treated sample.

We have now discovered that sustaining constitutive endothelial nitric oxide synthase (eNOS) activity can be used to inhibit platelet aggregation and clot retraction and/or to enhance fibrinolysis. During platelet aggregation and clot retraction, both inducible nitric oxide synthase (NOS) and constitutive endothelial nitric oxide synthase (eNOS) are transiently activated and then deactivated. While it was reported that calpeptin and IIbIIIa antagonists can inhibit inducible NOS, it was not known how to regulate constitutive eNOS activity. We have now found three different routes to sustain constitutive eNOS activity: (1) by inhibiting the activity of the syk kinase; (2) by inhibiting calpain; and (3) by using an antagonist of IIbIIIa.

One embodiment of the invention provides methods of treating thrombosis by inhibiting the activity of the syk kinase. A second embodiment of the present invention provides assays for the discovery of improved compounds to treat thrombosis, by screening for compounds which sustain eNOS activity, preferably constitutive eNOS activity. A third embodiment of the present invention provides assays for the discovery of improved compounds to treat thrombosis, by identifying inhibitors of calpain and IIbIIIa by screening for compounds which act through calpain or IIbIIIa to sustain eNOS activity, preferably constitutive eNOS.

Thrombus and Blood Clotting Disorders

Clotting as a result of an injury to a blood vessel is a critical physiological process for mammals such as man, and can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

One embodiment of the invention provides methods, kits, and compounds to sustain constitutive eNOS activity to inhibit platelet aggregation. Another embodiment of the invention provides methods, kits, and compounds to sustain constitutive eNOS activity to inhibit clot retraction. Yet another embodiment of the invention provides methods, kits, and compounds to sustain constitutive eNOS activity to promote fibrinolysis.

The kits, compounds, and methods of the present invention can be used for the treatment and prevention of a variety of thrombotic conditions including coronary artery and cerebrovascular disease. The present invention can inhibit the formation of blood platelet aggregates, inhibit the formation of fibrin, inhibit thrombus formation, and inhibit embolus formation in a mammal, in blood, in blood products, and in mammalian organs. The methods, kits, and compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The methods, kits, and compounds can also be used in prophylactic treatment of subjects who are at risk of developing such disorders. The methods, kits, and compounds can be used to lower the risk of atherosclerosis. The present invention can also be useful in prevention of cerebral vascular accident (CVA) or stroke.

Besides being useful for human treatment, these methods are also useful for veterinary treatment of companion animals, exotic animals and farm animals, including mammals, rodents, and the like. More preferred animals include horses, dogs, and cats.

The invention is useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with the present invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, the present invention is useful for maintaining patency of indwelling catheters.

Examples of cardiogenic thromboembolism which may be treated or prevented with the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis which may be treated or prevented with the invention include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, the invention is useful for maintaining patency in arteriovenous cannulas.

Examples of atherosclerosis which may be treated or prevented with the invention include arteriosclerosis.

The present invention is also useful for treating or preventing thrombosis associated with cancer and cancer chemotherapy in humans and other mammals.

Inhibition of syk Kinase

One embodiment of the invention provides methods of treating thrombosis by inhibiting the activity of the syk kinase. As described above, syk is one of several cellular kinases activated during platelet activation, by directly associating with the integrin $\alpha_{IIb}\beta_3$ in platelets. We have now discovered that eNOS activity is sustained in the presence of syk inhibitors, for example piceatannol.

One embodiment of the invention provides methods, kits, and compounds to sustain constitutive eNOS activity to inhibit platelet aggregation by inhibiting the activity of the syk kinase. Another embodiment of the invention provides methods, kits, and compounds to sustain constitutive eNOS activity to inhibit clot retraction by inhibiting the activity of the syk kinase. Yet another embodiment of the invention provides methods, kits, and compounds to sustain constitutive eNOS activity to promote fibrinolysis by inhibiting the activity of the syk kinase.

The activity of syk kinase can be inhibited using an agent that inhibits its function. One preferred inhibitor of syk is the plant natural product, piceatannol [Oliver, J. M. et al., J. Biol. Chem., 269: 29697-29703 (1994)]. Other inhibitors of syk are the pyrimidine-5-carboxamide derivatives described in U.S. Pat. No. 6,432,963. In one preferred embodiment, the syk kinase inhibitor is used to inhibit platelet aggregation and is not piceatannol.

In one preferred embodiment, the syk inhibitor is a peptide inhibitor, as described in U.S. Pat. No. 5,858,981. The peptide inhibitor of the invention, or mimetic thereof, can be introduced into target cells directly, for example, using liposomes. See also approaches described in Science 26:1877 (1993) for administration of peptides modified so as to render them capable of crossing cellular lipid membranes. Alternatively, a DNA sequence encoding the peptide inhibitor can be introduced using gene therapy protocols so that the peptide is produced intracellularly.

Suitable syk inhibitors include specific syk inhibitors, syk interference RNA, antibodies to syk or antigenic fragments thereof, intrabodies against syk, antisense oligonucleotides that inhibit syk expression and synthesis syk decoys such as dominant negative syk protein, and any organic or inorganic molecule designed to interfere with the activity of syk. Preferably one uses a single chain antibody as a syk inhibitor. One can also prepare or screen for other ligands that bind to syk.

Antibodies have long been used in biomedical science as in vitro tools for the identification, purification and functional manipulation of target antigens. Antibodies have been exploited in vivo for both diagnostic and therapeutic applications. Recent advances in antibody engineering have now allowed the gene encoding antibodies to be manipulated so that the antigen biding domain can also be expressed intracellularly. The specific and high-affinity binding properties of antibodies, combined with the ability to create large human immunoglobulin libraries and their ability to be stably expressed in precise intracellular location inside mammalian cells, has provided a powerful new family of molecules which can be used in gene therapy. These intracellular antibodies are called "intrabodies" (Marasco et al. Gene Therapy, 4:11-15, 1997; U.S. Pat. Nos. 5,965,371; 5,851,829; 6,329,173; and 6,072,036). Preferably nucleic acids encoding syk function as interfering intrabodies, encoded by a single chain antibody. Such antibodies include human and humanized antibodies against syk. Preparation and production of antibodies is well within the skill in the art.

Syk activity or function may also be inhibited using antisense nucleic acid technology. Antisense nucleic acids and oligonucleotides targeted against syk useful according to the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, for example, Weintraub, H. et al., Antisense RNA as a molecular tool for genetic analysis, Reviews—Trends in Genetics, Vol. 1 (1) 1986.

Further, catalytic RNAs can be used to reduce the amount of syk in cells. Catalytic RNAs having a specific syk ribonuclease activity can be selected from a pool of RNA molecules prepared using methods known to one skilled in the art. See, for example, Bartel, D. and Szostak, J. W. Science 261: 1411-1418 (1993).

Aptamers targeting syk may also be used to reduce the amount and therefore activity of syk in cells. Such aptamers can be produced using the methodology disclosed, for example, in U.S. Pat. No. 5,270,163 and WO 91/19813.

Syk antisense oligonucleotide and siRNA sequences can be readily designed by one skilled in the art using the syk nucleic acid sequences.

The term "dominant negative syk protein" or "syk decoy" as used herein refers to a syk protein which has been modified so that it will compete with the wild type syk but is incapable of the catalytic reaction. In one preferred embodiment, the dominant negative form of syk has the syk amino and/or carboxyl terminal ends but lacks or has a defective catalytic domain. For example, useful decoys according to the present invention are syk mutants designed to interfere with the function of the catalytic domain. Such syk decoys may be delivered into a cell using any method known to one skilled in the art that will accomplish the goal including genetic engineering and direct delivery of proteins or nucleic acids without genetic engineering. For example, if the syk decoy is a protein, a method such as described in Kreis et al. (EMBO J. 5:931-941, 1986), may be used. Kreis describes a method by which a protein can be injected intracellularly using microinjection. Another method of delivering a protein intracellularly uses endocytosis to have the protein enter the cell, for example, chemical conjugates containing an antibody conjugated to the protein (i.e., syk) desired to be delivered into the cell. The antibody is intended to bind extracellularly to the cell, and the process of endocytosis results in bringing the desired protein into the cell. See particularly FIG. 1 of Oeltmann and Frankel, FASEB J. 5:2334-2337 (1991)) and Seetharam et al. (J. of Biol. Chem 266:17376-17381 (1991)).

Modification of a cell to express a syk dominant negative construct can be achieved using transient or stable transfection methods well known to one skilled in the art. Examples of detailed protocols to prepare cell lines either for transient or stable expression are given, for example, in Molecular Cloning: A Laboratory Manual 3rd Ed., Sambrook and Russel, Cold Spring Harbor Laboratory Press, 2001.

Small interfering RNA technology (RNAi, siRNA) has been shown to be a powerful tool for manipulating gene expression in cells (Hannon, Nature 418:244-251, 2002). The technology arose from the observation that exogenous double-stranded RNAs induce gene silencing in plants and *Caenorhabditis elegans*. These double-stranded RNAs are processed into small interfering RNAs (siRNAs), which are incorporated into a conserved cellular machinery that mediates the suppression of homologous genes. Recently, small non-coding RNAs have been identified that can act as endogenous regulators of gene expression. These microRNAs typically form stem-loop structures, essentially short double-stranded RNAs, that enter the RNAi pathway (Knight et al., Science 293:2269-2271, 2001; Ketting et al., Genes Dev, 15:2654-2659, 2001; Hutvagner et al., Science 293:834-838, 2001; Grishok, et al., Cell 106:23-34, 2001). siRNAs, modeled after microRNAs, can be expressed from viral vectors to induce stable suppression of gene expression in cultured mammalian cells (Paddison and Hannon, Cancer Cell 2:17-23, 2002) and in various tissues in vivo (Add Refs: McCaffrey A P, et al (2002) Nature 418, 38-39; Lewis D L et al (2002) Nat Genetics 32, 107-108). Methods for preparing and delivering sequence specific, such as syk sequence specific interference RNAs into cells are presented, for example, in the US Patent Application No. 20020162126, which is herein incorporated by reference in its entirety.

Therefore, in one embodiment of the present invention, an siRNA targeting syk is introduced into the erythroid or erythroid progenitor cells, or stem cells capable of differentiating into erythroid cells. The cells are preferably isolated from the individual in need of treatment. The sequence specific dsRNA construct constituting the siRNA may be directly introduced into the cell (i.e., intracellularly); or introduced extracellularly into a cavity, interstitial space, into the circulation of the individual or introduced orally. Methods for oral introduction include direct mixing of RNA with food of the organism, as well as engineered approaches in which a species that is used as food is engineered to express an RNA, then fed to the individual. Physical methods of introducing nucleic acids include injection directly into the cell, gene or extracellular injection into the individual of an RNA solution. The double-stranded structure may be formed by a single self-complementary RNA strand or two complementary RNA strands. RNA duplex formation may be initiated either inside or outside the cell. siRNAs can also be delivered using viral vectors, including, but not limited to, retroviral and adenoviral vectors, which may either be replication defective, conditionally replicating or replication sufficient.

Compounds that inhibit syk can be formulated as pharmaceutical compositions and administered to a mammalian host, such as a human patient in a variety of forms adapted to the chosen route of administration, i.e., orally or parenterally, by intravenous, intramuscular, topical or subcutaneous routes. The present invention also provides kits containing syk inhibitors.

Discovery of Novel Compounds which Sustain eNOS Activity

We have now discovered that sustaining eNOS activity is a potent anti-thrombotic treatment. Accordingly, the invention provides assays for the discovery of improved compounds to treat thrombosis, by screening for compounds which sustain eNOS activity. Preferably the eNOS activity sustained is constitutive eNOS activity.

Assays for measuring nitric oxide synthase activity are well known in the art. For example, one preferred assay is a cell-based nitric oxide synthase assay employing the measurement of nitric oxide oxidation product, nitrite, in the conditioned medium of cultured cells. Preferably, the murine monocytic cell lines RAW 264.7 and J774 are used, as they are well documented as capable of producing >10 µM nitrite in response to immunostimulation.

Those skilled in the art will also recognize that there are numerous other assays for the activity of the NOS isoforms (including eNOS) which can be used to screen the biological activity of the compounds to identify compounds which sustain eNOS activity. These include assays for native NOS isoforms in tissues studied ex vivo (Mitchell et al., Br. J. Pharmacol. (1991), Vol. 104, pp. 289-291; Szabo et al., Br. J. Pharmacol. (1993), Vol. 108, pp. 786-792; Joly et al., Br. J. Pharmacol. (1995), Vol. 115, pp. 491-497) as well as primary cell cultures and cell lines (Forstermann et al., Eur. J. Pharmacol. (1992), Vol. 225, pp. 161-165; Radmoski et al., Cardiovasc. Res. (1993), Vol. 27, pp. 1380-1382; Wang et al., J. Pharmacol. Exp. Ther. (1994), Vol. 268, pp. 552-557). Those skilled in the art will also recognize that recombinant NOS enzymes can be expressed in heterologous cells by either transient transfection (Karlsen et al., Diabetes, (1995), Vol. 44, pp. 753-758), stable transfection (McMillan et al., Proc. Natl. Acad. Sci. (1992), Vol. 89, pp. 11141-11145; Sessa et al., J. Biol. Chem. (1995), Vol. 270, pp. 17641-17644) or via the use of lytic virus transfection (Busconi & Michel, Mol. Pharmacol. (1995), Vol. 47, pp. 655-659; List et al., Biochem. J. (1996), Vol. 315, pp. 57-63) using NOS cDNAs. Heterologous expression can be achieved in mammalian cells (McMillan et al., Proc. Natl. Acad. Sci. (1992), Vol. 89, pp. 11141-11145), insect cells (Busconi & Michel, Mol. Pharmacol. (1995), Vol. 47, pp. 655-659; List et al., Biochem. J. (1996), Vol. 315, pp. 57-63), yeast (Sari et al., Biochemistry (1996), Vol. 35, pp. 7204-7213) or bacteria (Roman et al., Proc. Natl. Acad. Sci. (1995), Vol. 92, pp. 8428-8432; Martasek et al., Biochem. Biophys. Res. Commun. (1996), Vol. 219, pp. 359-365). Any of these heterologous expression systems can be used to establish iNOS, nNOS and eNOS assay systems to evaluate the biological activity of the compounds of the present invention.

The effect of any compound identified as sustaining eNOS activity can be further characterized for its effect on platelet aggregation.

Platelets can be isolated and purified using any techniques known in the art. See for example Rooney et al., J. Biol. Chem. 271:8553-5 (1996). In one preferred embodiment, platelets can be purified from the whole blood of volunteers who have abstained from using aspirin for at least 10 days.

Platelet rich plasma can be obtained by centrifugation of collected blood, for example at 200 g for 25 minutes at ambient temperature. Platelets can be pelleted from the supernatant by centrifugation at 800 g for 20 minutes at ambient temperature, and resuspended in Tyrode's buffer, pH 7.2. Isolated platelets can be filtered through a Sepharose CL-2B column equilibrated with Tyrode's buffer, and eluted in the same buffer.

Platelets can be aggregated using any techniques known in the art. In one preferred method for platelet aggregation, platelets can be incubated at 37° C. at a final concentration of $1\times10^8$ platelets per 0.5 ml in cuvettes in a Chrono-log aggregometer. Aggregation can be initiate by the stepwise addition of 300 nM human plasma fibrinogen and agonist (10 μM ADP or 0.5 unit/ml thrombin), followed by stirring. Aggregation can be monitored as the increase in light transmission, and the aggregation reaction can be stopped after 20 s by the addition of 125 μl of ice-cold 5× lysis buffer.

Platelets can be stimulated using any agent that results in platelet activation, modeling platelet adhesion and thrombus formation. In one embodiment, platelets are stimulated by von Willebrand factor and ristocetin.

In the methods of the present invention, a variety of test compounds from various sources can be screened for the ability of the compound to sustain eNOS activity. Compounds to be screened can be naturally occurring or synthetic molecules. Compounds to be screened can also be obtained from natural sources, such as, e.g., marine microorganisms, algae, plants, fungi, etc. Alternatively, test compounds can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Test compounds can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, chimeric molecules, etc.

Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. In the method of the present invention, the preferred test compound is a small molecule, nucleic acid, peptide, protein, glycoprotein, carbohydrate, lipid, or glycolipid. Preferably, the nucleic acid is DNA or RNA.

Large combinatorial libraries of compounds can be constructed by the encoded synthetic libraries (ESL) method described in Affymax, WO 95/12608, Affymax WO 93/06121, Columbia University, WO 94/08051, Pharmacopeia, WO 95/35503 and Scripps, WO 95/30642 (each of which is incorporated herein by reference in its entirety for all purposes). Peptide and antibody libraries can also be generated by phage display methods. See, e.g., Devlin, WO 91/18980. Compounds to be screened can also be obtained from governmental or private sources, including, e.g., the DIVERSet E library (16,320 compounds) from ChemBridge Corporation (San Diego, Calif.), the National Cancer Institute's (NCI) Natural Product Repository, Bethesda, Md., the NCI Open Synthetic Compound Collection, Bethesda, Md., NCI's Developmental Therapeutics Program, or the like. Assays to Identify Calpain and IIb/IIIa Inhibitors which Sustain eNOS Activity Yet another embodiment of the present invention provides assays for the discovery of improved compounds to treat thrombosis, by identifying inhibitors of calpain and GPIIb/IIIa by screening for compounds which act through calpain or IIbIIIa to sustain eNOS activity, preferably constitutive eNOS activity.

During platelet aggregation and clot retraction, both inducible nitric oxide synthase (NOS) and constitutive endothelial nitric oxide synthase (eNOS) are transiently activated and then deactivated. While it has been shown that calpeptin and IIbIIIa antagonists can inhibit inducible NOS, we have now discovered that such antagonists can also inhibit eNOS.

Accordingly, one embodiment of the present invention provides for the development of assays to identify improved compounds to treat thrombosis, by identifying compounds which function via inhibition of calpain to sustain eNOS activity. Such assays comprise two steps: first, identifying inhibitors of calpain, and second, screening those inhibitors to identify those compounds that sustain eNOS activity.

One embodiment of the invention provides methods, kits, and compounds to sustain constitutive eNOS activity to inhibit platelet aggregation by inhibiting the activity of calpain. Another embodiment of the invention provides methods, kits, and compounds to sustain constitutive eNOS activity to inhibit clot retraction by inhibiting the activity of calpain. Yet another embodiment of the invention provides methods, kits, and compounds to sustain constitutive eNOS activity to promote fibrinolysis by inhibiting the activity of calpain.

The activity of calpain can be inhibited using an agent that inhibits its function. One preferred inhibitor of calpain is calpeptin. In one preferred embodiment of the invention, calpeptin is used to promote fibrinolysis. In another preferred embodiment, the calpain inhibitor is used to promote fibrinolysis and is not calpeptin. Other inhibitors of calpeptin useful for inhibiting platelet aggregation are described in U.S. patent application Ser. No. 09/953,590, published as US 2002/0128434A1; U.S. patent application Ser. No. 09/847,872, published as US 2002/0115665; and U.S. Pat. No. 6,448,245. In one preferred embodiment, these inhibitors are used to promote fibrinolysis. In another preferred embodiment, the calpain inhibitor is used to promote fibrinolysis and is not one of these inhibitors.

Any assay for calpain activity can be used to screen for compounds which inhibit its activity. Such inhibitors are then further characterized for the ability to sustain eNOS activity, as described above.

Calpains are mammalian calcium-dependent neutral cysteine proteases. Calpains are referred to as cysteine proteases because they include a cysteine residue that plays a critical role in the catalytic process. In one preferred embodiment, the calpain inhibitor calpeptin is used for enhancing fibrinolysis.

Assays for calpain activity are well known in the art. For example, measuring calpain activity using N-succinyl-leu-tyr 7-amino-4-methylcoumarin as the specific peptide substrate. Fluorescence can be measured in a 96-well microplate format (Dyrex Technologies (UK), Middlesex) with a 380 nm excitation filter and 480 nm emission filter. Total volume for each well can be 300 microliters containing Hanks' Balanced Salt Solution 1.times.(Cellgro), 2 micromolar calcium chloride, and varying amounts of inhibitor and N-succinyl-ley-tyr-7-amino-4-methylcoumarin. Data consisting of relative fluorescence units (RFU) can be obtained every two minutes for 1 hour, and analyzed based on initial rate, defined as the slope of the increase of the obtained RFU value up to a maximum length of 10 minutes. Several different substrate concentrations, such as 01 .mu.M, 1 .mu.M, 10 .mu.M, 100 .mu.M can be tested.

Any compound which is identified as inhibiting calpain is then further screened for its ability to sustain eNOS activity, as described above.

In this embodiment of the present invention, a variety of test compounds from various sources can be screened for the ability of the compound to both inhibit calpain and sustain eNOS activity, as described above. Compounds to be screened can be naturally occurring or synthetic molecules. Compounds to be screened can also be obtained from natural sources, such as, e.g., marine microorganisms, algae, plants, fungi, etc. Alternatively, test compounds can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Test compounds can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, chimeric molecules, etc.

The present invention also provides for the development of assays to identify improved compounds to treat thrombosis, by identifying compounds which function via inhibition of GPIIb/IIIa to sustain eNOS activity. Such assays comprise a two steps: first, identifying inhibitors of GPIIb/IIIa, and second, screening those inhibitors to identify those compounds that sustain eNOS activity.

As used herein, the surface integrin GPIIb/IIIa is sometimes referred to as the platelet integrin $\alpha_{IIb}\beta_3$ or simply IIb/IIIa.

One embodiment of the invention provides methods, kits, and compounds to sustain constitutive eNOS activity to inhibit platelet aggregation by inhibiting IIb/IIIa. Another embodiment of the invention provides methods, kits, and compounds to sustain constitutive eNOS activity to inhibit clot retraction by inhibiting IIb/IIIa. Yet another embodiment of the invention provides methods, kits, and compounds to sustain constitutive eNOS activity to promote fibrinolysis by inhibiting IIb/IIIa.

IIb/IIIa can be inhibited using an agent that inhibits its function. One preferred inhibitor of calpain is calpeptin. Inhibitors of IIb/IIIa useful for inhibiting platelet aggregation by disrupting the binding of fibrinogen to its receptor, IIb/III include for example various benzoic acid and phenylacetic acid (U.S. Pat. No. 5,039,805); seven membered ring containing bicyclic compounds (PCT WO 93/00095); bicyclic compounds having fused six membered rings (quinazoline-3-alkanoic acid derivates) (EP 456835); nonpeptidyl integrin inhibitors which are bicyclic 6 and 7 membered fused ring systems (PCT WO 93/08174); 6,5-bicyclic compounds (PCT WO94/12478 and WO94/08962); novel oxoquinazolin derivatives (British Patent application GB 2276384). Furthermore, the design of non-peptidal inhibitors of fibrinogen-glycoprotein IIb/IIIa binding has been described (McDowell, et. al., supra.). In one preferred embodiment, such known IIb/IIIa inhibitors are used to promote fibrinolysis. In another preferred embodiment, the IIb/IIIa inhibitor is used to promote fibrinolysis and is not one of these inhibitors.

Any assay for GPIIb/IIIa activity can be used to screen for compounds which inhibit its activity. Such inhibitors are then further characterized for the ability to sustain eNOS activity, as described above.

GPIIb/IIIa antagonists are capable of acting as fibrinogen receptor antagonists, inhibiting both platelet aggregation and binding of fibrinogen to the platelet receptor.

Assays for GPIIb/IIIa activity are well known in the art. In one preferred assay, in-vitro biological activity of the compounds is monitored using a modified fibrinogen-GPIIb/IIIa ELISA based on the method of Nachman and Leung (J. Clin. Invest. 69:263-269 (1982)), which measures the inhibition of fibrinogen binding to purified human platelet GPIIbIIIa receptor. Human fibrinogen is prepared by the method of Lipinska, et al. (J. Lab. Clin. Med. 84:509-516 (1974)). Platelet GPII.sub.b III.sub.a is prepared by the method of Fitzgerald, et al., Anal. Biochem., 151:169-177 (1985). Briefly, microtiter plates are coated with fibrinogen (10 mg/ml) and then blocked with TACTS buffer containing 0.5% bovine serum albumin (BSA). (TACTS buffer contains 20 mM Tris.HCl, pH 7.5, 0.02% sodium azide, 2 mM calcium chloride, 0.05% Tween 20, 150 mM sodium chloride.) The plate is washed with phosphate buffered saline (PBS) containing 0.01% Tween 20 and the sample to be determined added, followed by addition of solubilized GP IIbIIIa receptor (40 mg/ml) in TACTS, 0.5% BSA. After incubation, the plate is washed and 1 mg/ml of murine anti-platelet monoclonal antibody AP3 (Newman et al., Blood 65:227-232 (1985)) is added. After another wash a goat anti-mouse IgG conjugated to horseradish peroxidase is added. A final wash is performed and developing reagent buffer (10 mg o-phenylenediamine dihydrochloride, 0.0212% hydrogen peroxide, 0.22 mM citrate, 50 mM phosphate, pH 5.0) is added and then incubated until color develops. The reaction is stopped with 1N sulfuric acid and the absorbance at 492 nm is recorded.

In addition to the GPII.sub.b III.sub.a ELISA assay, platelet aggregation assays may be performed in human platelet rich plasma (PRP). Fifty milliliters of whole human blood (9 parts) is drawn on 3.6% sodium citrate (1 part) from a donor who has not taken aspirin or related medications for at least two weeks. The blood is centrifuged at 160.times.g for 10 min at 22° C. and then allowed to stand for 5 min after which the PRP is decanted. Platelet poor plasma (PPP) is isolated from the remaining blood after centrifugation at 2000×g for 25 min. The platelet count of the PRP is adjusted to ca. 300,000 per microliter with PPP. A 225 mL aliquot of PRP plus 25 mL of either a dilution of the test sample or a control (PBS) is incubated for 5 min in a Chrono-log Whole Blood Aggregometer at 25° C. An aggregating agent (collagen, 1 mg/ml; U46619, 100 ng/ml; or ADP, 8 mM) is added and the platelet aggregation recorded.

Any compound which is identified as inhibiting GPIIb/IIIa is then further screened for its ability to sustain eNOS activity, as described above.

In this embodiment of the present invention, a variety of test compounds from various sources can be screened for the ability of the compound to both inhibit GPIIb/IIIa and sustain eNOS activity, as described above. Compounds to be screened can be naturally occurring or synthetic molecules. Compounds to be screened can also be obtained from natural sources, such as, e.g., marine microorganisms, algae, plants, fungi, etc. Alternatively, test compounds can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Test compounds can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, chimeric molecules, etc.

Compounds that inhibit GPIIb/IIIa or calpain can be formulated as pharmaceutical compositions and administered to a mammalian host, such as a human patient in a variety of forms adapted to the chosen route of administration, i.e., orally or parenterally, by intravenous, intramuscular, topical or subcutaneous routes. The present invention also provides kits containing GPIIb/IIIa or calpain inhibitors.

Administration

Administration of the compositions of the present invention to the patient includes both self-administration and administration to the patient by another person.

Additional active agents may be used in combination with the compounds of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and anti-oxidant vitamins such as vitamin C and E and beta carotene.

The compounds of the present invention can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin and simvastatin, IMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of compounds of the invention in combination with other suitable anti-platelet agents, anticoagulation agents, or thrombolytic agents may be the same as those doses of the present compounds administered without coadministration of additional anti-platelet agents, anticoagulation agents, or thrombolytic agents, or may be substantially less that those doses of the present compounds administered without coadministration of additional anti-platelet agents, anticoagulation agents, or thrombolytic agents, depending on a patient's therapeutic needs.

In one preferred embodiment, the compositions of the present invention can be used in connection with devices that come into contact with blood. Examples of devices that come into contact with blood include vascular grafts, stents, orthopedic prosthesis, cardiac prosthesis, and extracorporeal circulation systems.

The compounds of the present invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with a fine inert powdered carrier and inhaled by the subject or insufflated. Such compositions and preparations should contain at least 0.1% of the active agent or compound. The percentage of the compositions and preparations may, of course, be varied and may conveniently be between about 2 to about 60% of the weight of a given unit dosage form. The amount of agent or compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound may be incorporated into sustained-release preparations and devices.

The agents and compounds of the present invention may also be administered intravenously or intraperitoneally by infusion or injection. Solutions of the compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the compound which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound of the present invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compound may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water-alcohol/glycol blends, in which the agent can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound of the present invention is conveniently administered in unit dosage form; for example, containing 5 to 1000 mg, conveniently 10 to 750 mg, most conveniently, 50 to 500 mg of active ingredient per unit dosage form.

Ideally, the compound should be administered to achieve peak plasma concentrations of from about 0.5 to about 75 μM, preferably, about 1 to 50 μM, most preferably, about 2 to about 30 μM. This may be achieved, for example, by the intravenous injection of a 0.05 to 5% solution of the compound, optionally in saline, or orally administered as a bolus containing about 1-100 mg of the compound. Desirable blood levels may be maintained by continuous infusion to provide about 0.01-5.0 mg/kg/hr or by intermittent infusions containing about 0.4-15 mg/kg of the compound.

The compound may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The present invention provides kits containing one of the above-described forms of the compound and a pharmaceutically acceptable carrier, including instructions for how to use it to sustain constitutive eNOS activity, which can then be used in treating or preventing the ailments described above.

The present invention provides kits containing the compound and a pharmaceutically acceptable carrier, including the syk inhibitors, GPIIb/IIIa, or calpain inhibitors.

EXAMPLES

Example 1

Inhibition of Clot Retraction

To determine the effect of the syk kinase inhibitor piceatannol and the calpain inhibitor calpeptin, the following experiments were carried out. Platelets ($2 \times 10^8$ platelets/ml) were incubated with either piceatannol at a final concentration of 40 μg/ml, calpeptin at a final concentration of 200 μg/ml, or vehicle DMSO for 30 minutes in the dark. To each sample, fibrinogen was added to a final concentration of 300 nM, 1 mM $Ca^{2+}$, and 2 mM $Mg^{2+}$, 10 minutes prior to the addition of 0.5 unit/ml of thrombin. The clots were incubated for 30 minutes at 37° C. and then transferred to ice before taking photographs. Tubes: 1, vehicle control treated sample without the addition of thrombin; 2, vehicle control treated sample; 3, piceatannol treated sample; 4, calpeptin treated sample.

Piceatannol at 20 ug/ml and 40 ug/ml inhibited clot retraction where as PP2 at 10 μM did not. As shown in FIG. 1, no clot retraction was observed in tube 1 when thrombin was not added which served as a negative control. Tube 2 showed a retracted clot which is like a small white thread hanging in the tube. Tubes 3 and 4 do not contain this retracted clot, suggesting that piceatannol at 40 ug/ml and calpeptin 200 ug/ml inhibited platelet mediated clot retraction. Results from other experiments showed that Piceatannol at 20 ug/ml was also able to inhibit clot retraction but 10 ug/ml piceatannol was not that effective (data not shown). 10 uM PP2, a specific inhibitor of src kinase did not have any effect on clot retraction (data not shown). This concentration of this inhibitor is reported to inhibit src kinase. Thus, piceatannol mediated inhibition of clot retraction seems due to the inhibition of syk kinase.

This result indicates that piceatannol mediated clot retraction is due to syk kinase inhibition and not due to src kinase inhibition as src kinase specific inhibitor PP2 failed to show any inhibition. Calpeptin at 200 μg/ml inhibited clot retraction (FIG. 1), which shows that calpain inhibition also blocks clot retraction.

Example 2

Nitric Oxide Production

Figure 2B:
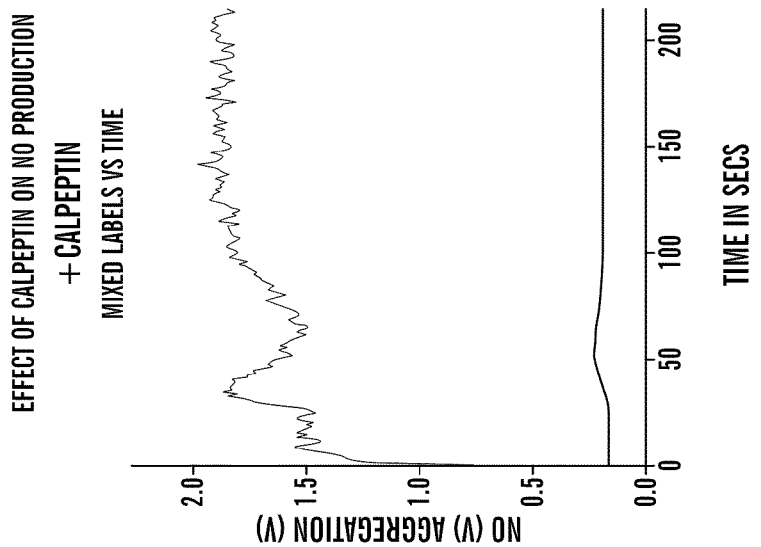
FIGS. 2A and 2B show the effect of calpeptin on NO production. Platelets at $2\times10^8$/ml were pre-incubated with either calpeptin at final concentration 200 ug/ml or vehicle DMSO for 30 minutes in the dark. To a final volume of 0.5 ml, fibrinogen was added to a final concentration of 1 mg/ml, 1 mM $Ca^{2+}$, and 2 mM $Mg^{2+}$, and GPRP (gly-pro-arg-pro) to a final concentration of 20 µM. The tube was placed in the NO-501 monitor to measure NO production and the platelets are stirred with a magnetic stirrer. TRAP (Thrombin Receptor Agonist Peptide) at a final concentration of 20 µM was added to start the reaction. The red line shows the platelet NO production and the blue line platelet aggregation. The readings were taken for 300 seconds (5 minutes).
Figure 2A:
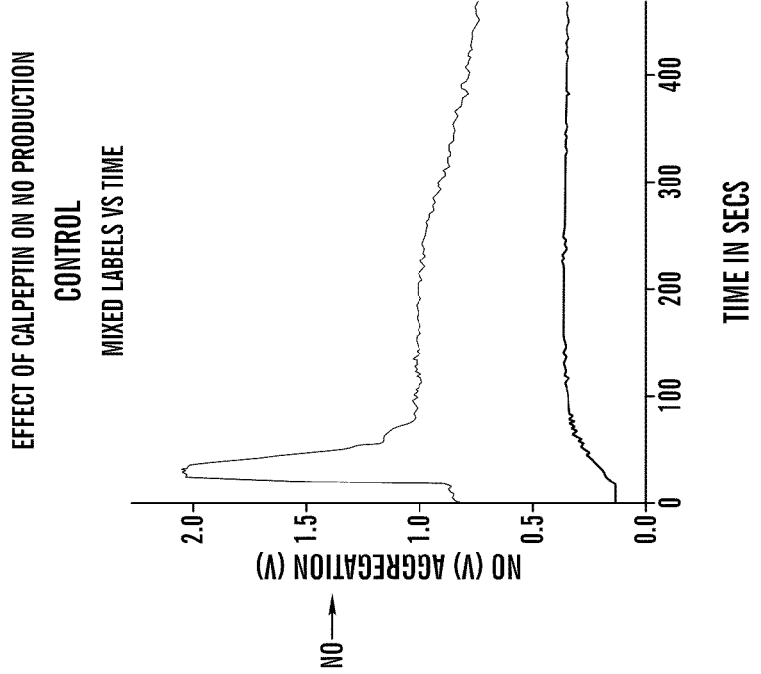

FIG. 2 shows the effect of calpeptin on NO production. Platelets at $2\times10^8$/ml were pre-incubated with either calpeptin at final concentration 200 ug/ml or vehicle DMSO for 30 minutes in the dark. To a final volume of 0.5 ml, fibrinogen was added to a final concentration of 1 mg/ml, 1 mM $Ca^{2+}$, and 2 mM $Mg^{2+}$, and GPRP to a final concentration of 20 μM. The tube was placed in the NO-501 monitor to measure NO production and the platelets are stirred with a magnetic stirrer. TRAP (Thrombin Receptor Agonist Peptide) at a final concentration of 20 μM was added to start the reaction. The red line shows the platelet NO production and the blue line platelet aggregation. The readings were taken for 300 seconds (5 minutes).

Calpeptin at 200 μg/ml increased and sustained NO production. In vitro experiments have shown that increased NO production inhibited platelet recruitment. FIG. 2 showed that protease calpain inhibitor Calpeptin increased and sustained NO production (compare right panel with the left) from platelets at the same concentration it inhibits both platelet aggregation and clot retraction. We conclude that enhanced and sustained NO production by endothelial nitric oxide present in platelets (eNOS) at least may be one of the reasons if not the sole reason for the inhibition platelet aggregation and clot retraction when calpain activation is inhibited.

FIG. 3 shows the effect of piceatannol on NO production. Platelets at $2\times10^8$/ml were pre-incubated with either piceatannol at final concentration 2.5 μg/ml or vehicle DMSO for 30 minutes in the dark. To a final volume of 0.5 ml, fibrinogen was added to a final concentration of 1 mg/ml, 1 mM $Ca^{2+}$, and 2 mM $Mg^{2+}$, and GPRP to a final concentration of 20 μM. The tube was placed in the NO-501 monitor to measure NO production and the platelets were stirred with a magnetic stirrer. TRAP (Thrombin Receptor Agonist Peptide) at a final concentration of 20 μM was added to start the reaction.

Piceatannol even at 5 μg/ml produced that much amount of NO which was out of scale. We were able to measure NO production at 2.5 μg/ml which was sustained and increased with time.

The right panel of FIG. 3 clearly shows that piceatannol even at concentration as low as 2.5 μg/ml sustained and increased NO production up to 5 minutes. Control was monitored for only up to 200 seconds, as it was obvious from the figure that there would be no further increase in NO production after the initial rapid and transient increase which is typical for normal platelets. The increase in platelet aggregation as shown in FIG. 2 with time, was also accompanied with a decrease in NO production.

Example 3

Clot Lysis

Anti-thrombotic agents can block or inhibit thrombus formation but they are not much effective on pre-formed thrombus to dissolve them and/or to help in fibrinolysis at t-PA or u-PA. Thus terminally full thrombus formation may cause myocardial-infarction (heart attack) and/or ischemic chest pain. The treatment for total blockage by thrombus formation is so far either angio-baloon-plasty and/or by-pass surgery. Fibrinolytic agents do not usually work as plasma plasminogen could not be converted to plasmin as active platelets at the site of thrombus formation secrete molecules such as PAI which inhibit proteolytic processing of plasminogen to generate active plasmin.

To assess the effect of piceatannol and calpeptin on the fibrinolytic effect of t-PA and plasminogen in the presence of platelets, we designed a two step procedure by modifying the fibrinolytic assay as described by Fay et al. (Blood, 83, 351-356, 1994).

First, we developed a retracted clot in the presence of fluorescence tagged fibrinogen in tubes containing platelets by the addition of thrombin. The residual fluid was taken out and platelets were added to each tube either treated with piceatannol, calpeptin and the vehicle control DMSO respectively. Glu-plasminogen, t-PA were added and the reaction was started by the addition of thrombin. After 90 minutes, the fluid from each tube was taken out and put in separate microfuge tubes followed by centrifugation. The detection of fluorescence in the supernatant was a measure of clot lysis.

Piceatannol at 40 μg/ml and calpeptin at 200 μg/ml increased fibrinolysis of clots made in the presence of platelets and lysis assay done in the presence of platelets, up to about 600% (6.2 times) of that of the control (Table 1). Normally, it is very difficult to achieve clot lysis in the presence of platelets. The control sample without treatment showed negligible clot lysis as expected. The value in control was designated as 1 to get comparative values for the treated samples.

TABLE 1

| Clot Lysis in the Presence of Platelets | |
|---|---|
| Control | 1 |
| Piceatannol 40 ug/ml | 6.2 |
| Calpeptin 200 ug/ml | 6.2 |

To form the clot, Oregon green 488 conjugated fibrinogen (fluorescent, from Molecular Probe) at 300 nM final concentration, 1 mM $Ca^{2+}$, 2 mM $Mg^{2+}$, was added to platelets at $2\times10^8$/ml concentration in 0.5 ml. The clot retraction was started with the addition of 0.5 unit/ml thrombin. The tubes were kept at 37° C. in dark for 1 hour until the clot retraction was complete. The residual fluid was taken out from each tube.

To initiate clot lysis, platelets at $2\times10^8$/ml concentration were treated with either 40 ug/ml piceatannol, 200 ug/ml calpeptin or vehicle DMSO. In 0.25 ml of each, Glu-plasminogen was added to a final concentration of 20 μg/ml, and t-PA was added to a final concentration of 2 U/ml. The reaction was started with the addition of thrombin at final concentration of 0.5 U/ml. The tubes were kept at 37° C. for 90 minutes. The fluid from each tube was taken in separate microfuge tubes and centrifuged at cold at 14000 rpm for 10 minutes. The supernatants were isolated. Each supernatant was diluted to 5 times and fluorescence in each sample was measured at excitation: 495 nm and emission: 525 nm.

This is the first demonstration of successful clot lysis in the presence of platelets. Clot lysis was obtained due to the inhibition of syk and protease calpain respectively. The mechanism of inhibition is under investigation. It is possible that the enhanced formation of plasmin from plasminogen by t-Pa may be facilitated by the enhanced and sustained production of NO. Alternatively, these agents may regulate key secretory proteins which may modulate plasmin formation from plasminogen by t-PA.

Taken together, these results show that inhibition of either syk kinase or the protease calpain: (i) enhanced and sustained the production of NO in platelets; (ii) inhibited clot retraction; and (iii) enhanced clot lysis. Thus, inhibition of syk activation and calpain activation in platelets is useful for preventing thrombotic events as well as promoting fibrinolytic events.

All references described herein are incorporated herein by reference.

We claim:

1. A method of identifying a compound useful in the treatment of a thrombotic condition, comprising screening a library of candidate compounds to identify those compounds which sustain constitutive endothelial nitric oxide synthase activity during platelet aggregation.

2. A method of identifying a compound useful in the treatment of a thrombotic condition, comprising screening a library of candidate compounds to identify those compounds which inhibit calpain and sustain constitutive endothelial nitric oxide synthase activity during platelet aggregation.

3. A method of identifying a compound useful in the treatment of thrombosis, comprising screening a library of candidate compounds to identify those compounds which inhibit GPIIb/IIIa and sustain constitutive endothelial nitric oxide synthase activity during platelet aggregation.

4. An in vitro assay to identify a compound to promote fibrinolysis in the presence of platelets, comprising identifying an agent which inhibits calpain activity, wherein the agent which inhibits calpain activity sustains endothelial nitric oxide synthase activity.

5. An in vitro method to identify a compound which promotes fibrinolysis in the presence of platelets comprising,
   (a) screening a library of compounds in a calpain assay to identify an agent which inhibits calpain activity; and
   (b) screening the agent identified in step (a) in a nitric oxide synthase assay to identify an agent which sustains endothelial nitric oxide synthase activity, wherein an agent which inhibits calpain activity and sustains endothelial nitric oxide synthase activity promotes fibrinolysis in the presence of platelets.

6. The method of claim 5, wherein the endothelial nitric oxide synthase activity is constitutive eNOS activity.

7. The method of claim 4, wherein both an inhibitor of a syk kinase and an inhibitor of calpain is identified.

* * * * *